United States Patent
Wei et al.

(10) Patent No.: US 10,253,011 B1
(45) Date of Patent: Apr. 9, 2019

(54) LUBIPROSTONE CRYSTALS AND METHODS FOR PREPARING THE SAME

(71) Applicant: CHIROGATE INTERNATIONAL INC., Yangmei (TW)

(72) Inventors: Shih-Yi Wei, Yangmei (TW); Jian-Bang Jheng, Yangmei (TW)

(73) Assignee: CHIROGATE INTERNATIONAL INC., Yangmei (TW)

( * ) Notice: Subject to any disclaimer, the term of this patent is extended or adjusted under 35 U.S.C. 154(b) by 0 days.

(21) Appl. No.: 16/034,686

(22) Filed: Jul. 13, 2018

(51) Int. Cl.
*B01D 9/00* (2006.01)
*C07D 311/94* (2006.01)

(52) U.S. Cl.
CPC .......... *C07D 311/94* (2013.01); *B01D 9/0004* (2013.01); *B01D 9/0022* (2013.01); *B01D 9/0036* (2013.01); *B01D 2009/0086* (2013.01); *C07B 2200/13* (2013.01)

(58) Field of Classification Search
CPC .. C07D 311/94; B01D 9/0004; B01D 9/0022; B01D 9/0036; B01D 2009/0086; C07B 2200/13
USPC .......................................................... 546/396
See application file for complete search history.

(56) References Cited

U.S. PATENT DOCUMENTS

| | | | | |
|---|---|---|---|---|
| 2007/0244333 A1* | 10/2007 | Hirata | ............... | C07C 405/0025 549/305 |
| 2010/0056807 A1* | 3/2010 | Alberico | ............... | C07C 405/00 549/299 |
| 2010/0056808 A1 | 3/2010 | Alberico et al. | | |
| 2011/0028541 A1* | 2/2011 | Tang | ....................... | C07C 51/00 514/456 |
| 2012/0065409 A1* | 3/2012 | Kothakonda | ......... | C07C 69/734 549/214 |
| 2012/0309990 A1* | 12/2012 | Weeratunga | ......... | C07D 311/94 549/396 |
| 2013/0096325 A1* | 4/2013 | Ceccarelli | ............ | A61K 31/558 549/396 |
| 2013/0184476 A1* | 7/2013 | Jackson | ............... | C07D 311/94 549/396 |
| 2013/0225842 A1* | 8/2013 | Henschke | ............. | C07C 29/143 549/396 |
| 2016/0009740 A1* | 1/2016 | Henschke | ............. | C07F 7/1892 556/441 |
| 2016/0237056 A1* | 8/2016 | Yiannikouros | ....... | C07C 49/753 |
| 2018/0016230 A1* | 1/2018 | Zhao | ..................... | C07C 211/38 |

FOREIGN PATENT DOCUMENTS

| | | | |
|---|---|---|---|
| CN | 102020625 | * | 4/2011 |
| CN | 104710298 A | | 6/2015 |
| CN | 104710398 | * | 6/2015 |
| CN | 107474033 | * | 12/2017 |

(Continued)

OTHER PUBLICATIONS

Computer generated English translation of CN104710298A, Jun. 17, 2015.

(Continued)

*Primary Examiner* — Daniel R Carcanague
(74) *Attorney, Agent, or Firm* — Ladas & Parry LLP

(57) ABSTRACT

This present invention relates to novel Lubiprostone crystals and methods for preparing the same. The preparation methods provided by the invention can effectively reduce or eliminate impurity in the obtained Lubiprostone crystals.

20 Claims, 12 Drawing Sheets

(56) References Cited

FOREIGN PATENT DOCUMENTS

| | | | |
|---|---|---|---|
| CN | 108503619 | * | 9/2018 |
| WO | 2009121228 A2 | | 10/2009 |
| WO | 2011091513 A1 | | 4/2011 |

OTHER PUBLICATIONS

Computer generated English translation of WO2009121228A2, Oct. 8, 2009.

* cited by examiner

LUBIPROSTONE CRYSTALS AND METHODS FOR PREPARING THE SAME

FIELD OF THE INVENTION

The present invention relates to novel Lubiprostone crystals and methods for preparing the same, and particularly relates to high purity Lubiprostone crystals and preparation methods thereof.

BACKGROUND OF THE INVENTION

Lubiprostone is an active pharmaceutical ingredient in the drug product Amitiza® for the treatment of diseases such as chronic idiopathic constipation, predominantly irritable bowel syndrome-associated constipation in women and opioid-induced constipation. Lubiprostone is categorized as a more unstable prostaglandin E1, and is easily and rapidly degraded to prostaglandin A1, hereinafter referred to as impurity A, under acid or alkaline conditions or even at room temperature as shown in the following Scheme A:

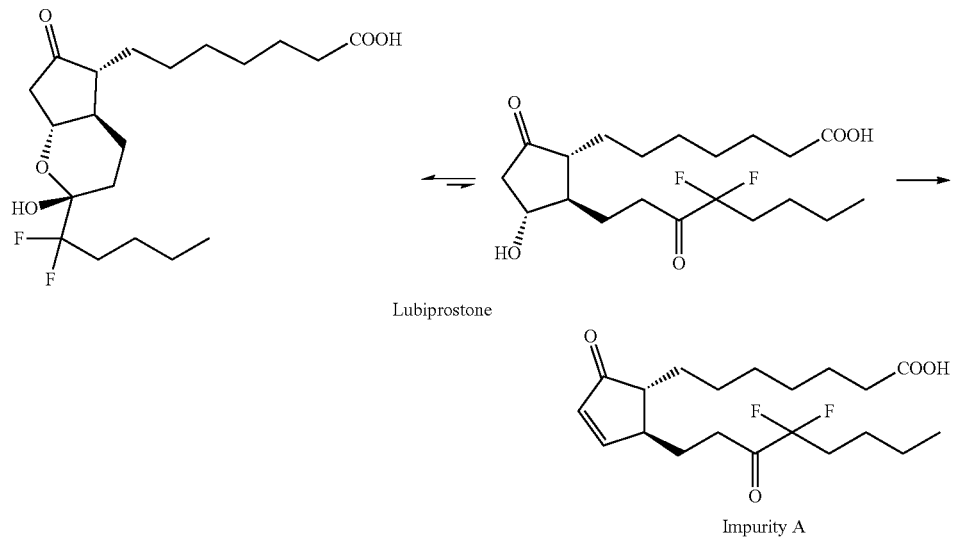

Scheme A

Lubiprostone

Impurity A

Therefore, both the preparation method and the purification process of Lubiprostone generate a certain amount of impurity A as shown in Scheme A. Impurity A has been identified as the major degradation products or impurity of Lubiprostone. Although impurity A can be removed by silica gel chromatography, additional impurities A will be regenerated in the purified Lubiprostone solution during the subsequent high-temperature, long-duration concentration process. Given this, it has been noted that the best final purification step for industrial mass production of Lubiprostone is crystallization, which does not require high temperatures or a long-duration concentration process.

Many prior art references show crystallization methods for Lubiprostone, but none discloses amounts of impurity A either before or after crystallization. The prior art references focus on the types of crystalline forms of Lubiprostone. Thus, the benefits of conventional crystallization methods for purifying Lubiprostone cannot be evaluated based on the prior art references.

For example, WO 2009/121228 discloses a crystalline form of Lubiprostone, hereinafter referred to as Lubiprostone crystal I, which can be obtained using various low boiling point solvent systems, such as ethyl acetate/n-hexane, acetone/n-hexane, dichloromethane/n-hexane, isopropanol/n-hexane, acetone/water, and methanol/water. Solvents with low boiling points have typically been used for crystallization because they are easily removed from the resultant crystals simply by allowing the solvent to evaporate. The Lubiprostone crystal I has an X-ray powder diffraction pattern as shown in FIG. 1 and a differential scanning calorimetry pattern comprising an endothermic peak with a peak onset temperature of 59.34° C. and a peak maximum of 60.97° C.

US 2010/056808 discloses a crystalline Lubiprostone, hereinafter referred to as Lubiprostone crystal II, obtained in a solvent system of isopropyl acetate/heptane. US 2010/056808 teaches that two crystallographically independent molecules, enantiomorphs, were found by optical microscope in the unit cell of Lubiprostone crystal II. US 2010/056808 further discloses that an ideal powder pattern was calculated from the single crystal data; this pattern is shown in FIG. 2 and FIG. 3 of the accompanying drawings. Upon comparison, it is found that the pattern shown in FIG. 3 is consistent with that of FIG. 1, so the polymorph B of Lubiprostone shown in FIG. 3 (i.e., FIG. 3 of US 2010/056808) might be the same as Lubiprostone crystal I. However, US 2010/056808 does not directly illustrate the X-ray powder diffraction spectrum of Lubiprostone crystal II. Moreover, US 2010/056808 neither teaches the amount ratios of the two enantiomorphs, nor indicates which enantiomorph is the crystalline form of Lubiprostone.

WO 2011/091513 discloses another crystalline form of Lubiprostone, i.e., APO-II, hereinafter referred to as Lubiprostone crystal III, which has an X-ray powder diffraction diffractogram as shown in FIG. 4 and a differential scanning calorimetry thermogram comprising an endothermic peak with a peak onset temperature of approximately 76° C. and a peak maximum of approximately 77° C.

CN 104710398 discloses a further Lubiprostone crystal form, hereinafter referred to as Lubiprostone crystal IV, which has an X-ray powder diffraction pattern as shown in FIG. 5 and a differential scanning calorimetry pattern comprising a peak maximum of 58±2° C.

Consequently, there is a demand for crystallization methods for the efficient and economical preparation of high-purity Lubiprostone crystals such that undesirable impurities, particularly impurity A, can be effectively reduced or avoided or can be easily removed during the crystallization purification method.

SUMMARY OF THE INVENTION

Based on the above background, the inventors of the present invention carried out a series of research studies, and found to their surprise that the use of the solvents with high boiling points can obtain novel crystalline forms of Lubiprostone with high purity. The present invention relates, at least in part, to two crystalline forms of Lubiprostone, one form being precipitated from o-xylene or m-xylene and termed Lubiprostone crystal V, and the other form being precipitated from p-xylene and termed Lubiprostone crystal VI, and to methods for preparing the Lubiprostone crystal V and the Lubiprostone crystal VI.

In one aspect, the present invention provides a method for preparing Lubiprostone crystal V, which comprises dissolving Lubiprostone in a first solvent selected from the group consisting of o-xylene, m-xylene, and a mixture thereof, to form a homogenous solution; lowering the temperature and/or adding to the homogenous solution a second solvent selected from the group consisting of pentane, hexane, heptane, octane, nonane, decane, cyclopentane, cyclohexane, cycloheptane, and mixtures thereof until a phase-separated fluid is formed at the bottom; pipetting out an upper clear solution and collecting the remaining phase-separated fluid; and evaporating off the phase-separated fluid under high vacuum until a precipitate is formed.

In one aspect, the present invention provides another method for preparing Lubiprostone crystal V, which comprises dissolving Lubiprostone in a third solvent selected from the group consisting of o-xylene, m-xylene, ethyl ether, isopropyl ether, methyl tert-butyl ether, and mixtures thereof to form a homogenous solution; lowering the temperature and/or adding to the homogenous solution a fourth solvent selected from the group consisting of pentane, hexane, heptane, octane, nonane, decane, cyclopentane, cyclohexane, cycloheptane, and mixtures thereof; adding a seed crystal of Lubiprostone crystal V; and stirring until a precipitate is formed.

In one aspect, the present invention provides a Lubiprostone crystal V having a X-ray powder diffraction (XRPD) pattern exhibiting its five strongest characteristic peaks at the following 2θ reflection angles: 6.5±0.2°, 13.2±0.2°, 15.6±0.2°, 18.9±0.2°, and 20.2±0.2°, wherein a half peak width of the characteristic peaks at 2θ reflection angles is between about 0.3° and about 2°.

In one aspect, the present invention provides a method for preparing Lubiprostone crystal VI, which comprises dissolving Lubiprostone in p-xylene to form a homogenous solution; lowering the temperature and/or adding to the homogenous solution a solvent selected from the group consisting of selected from the group consisting of pentane, hexane, heptane, octane, nonane, decane, cyclopentane, cyclohexane, cycloheptane, and mixtures thereof, and stirring until a precipitate is formed.

In one aspect, the present invention provides a Lubiprostone crystal VI having an XRPD pattern exhibiting its five strongest intensity peaks at the following 2θ reflection angles: 7.5±0.2°, 10.3±0.2°, 13.9±0.2°, 18.7±0.2°, and 21.1±0.2°.

In another aspect, the present invention provides novel Lubiprostone crystals useful for the production of high-purity Lubiprostone by crystallization.

DETAILED DESCRIPTION OF THE INVENTION

Lubiprostone Crystal V and Preparation Thereof

Figure 1:
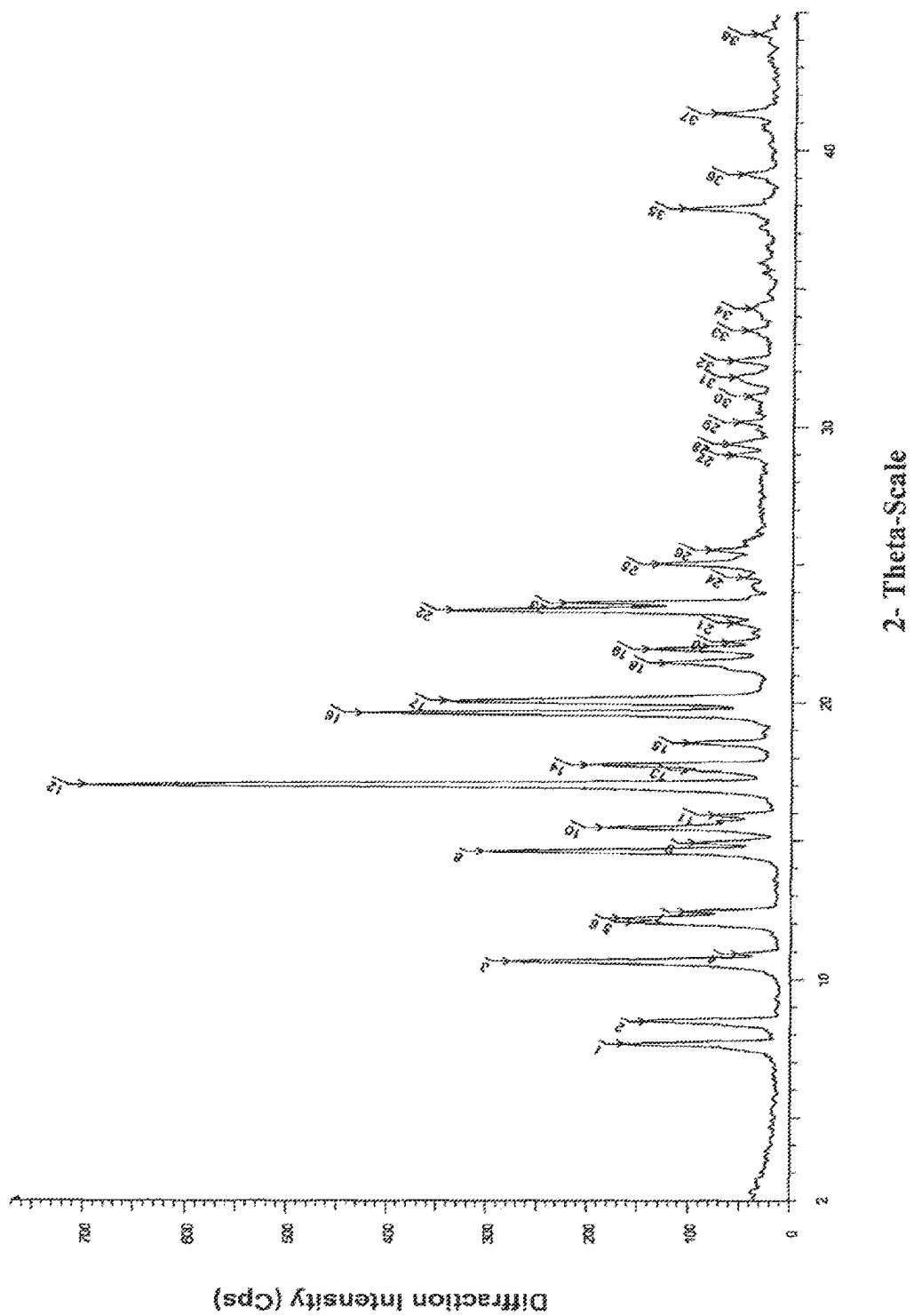
FIG. 1 shows an X-ray powder diffraction (XRPD) pattern of Lubiprostone crystal I.

In the present invention, the method for preparing Lubiprostone crystal V comprises the steps of:

(a) dissolving crude Lubiprostone in a first solvent selected from the group consisting of o-xylene, m-xylene, and a mixture thereof to form a homogenous solution;

(b) lowering the temperature and/or adding to the homogeneous solution a second solvent selected from the group consisting of pentane, hexane, heptane, octane, nonane, decane, cyclopentane, cyclohexane, cycloheptane, and mixtures thereof until a phase-separated fluid is formed at the bottom;

(c) pipetting out an upper clear solution and collecting the remaining phase-separated fluid;

(d) optionally adding a seed crystal of Lubiprostone crystal V;

(e) evaporating off the phase-separated fluid under high vacuum until a precipitate is formed;

(f) adding the second solvent to rinse the precipitate;

(g) filtering out the precipitate, thereby isolating the Lubiprostone crystal V; and (h) optionally drying the Lubiprostone crystal V.

The selection of the first solvent is the key to determine whether a crystalline form of Lubiprostone can be obtained and/or what kind of crystalline form of Lubiprostone is obtained. In the present invention, the first solvent used to dissolve the crude Lubiprostone is selected from the group consisting of o-xylene, m-xylene, and a mixture thereof, preferably o-xylene. The volume of the first solvent ranges from about 0.5 ml to about 10 ml, preferably about 1 ml to about 5 ml, and more preferably about 1.5 ml to about 4 ml, per 1 g of the crude Lubiprostone. The crude Lubiprostone can be dissolved in the first solvent at a temperature ranging from about 0° C. to about 80° C., preferably from about 20° C. to about 70° C., and more preferably from room temperature to about 60° C.

In a preferred embodiment, the second solvent is selected from the group consisting of pentane, hexane, heptane, octane, nonane, decane, cyclopentane, cyclohexane, cycloheptane, and mixtures thereof, and preferably n-pentane, n-hexane, cycloheptane, n-heptane, and mixtures thereof. The volume of the second solvent ranges from about 0.5 ml to about 30 ml, preferably about 1 ml to about 15 ml, and more preferably about 2 ml to about 10 ml, per 1 ml of the first solvent. The second solvent can be added at a temperature ranging from about −10° C. to about 80° C., preferably from about −5° C. to about 60° C., and more preferably from about 0° C. to about 30° C.

In one embodiment of the present invention, the temperature of the homogenous solution is lowered to a temperature ranging from about −10° C. to about 40° C., preferably from about 0° C. to about 30° C., and more preferably from about 10° C. to about 25° C.

In one embodiment of the present invention, the precipitation of the crystal can be performed at a temperature ranging from about −10° C. to about 40° C., preferably about 0° C. to about 30° C., and more preferably about 10° C. to about 25° C.

In one embodiment of the present invention, the step of evaporating off the phase-separated fluid can be performed under reduced pressure of about $10^{-4}$ Torr to about 25 Torr, preferably about $10^{-2}$ Torr to about 10 Torr, and preferably about $10^{-1}$ Torr to about 1 Torr.

The aforementioned method can directly produce novel Lubiprostone crystal V, which is essentially a single crystalline form and does not contain any other crystalline forms of Lubiprostone, without the addition of any crystal seeds. The Lubiprostone crystal V thereby obtained can be used as crystal seeds for copying Lubiprostone crystal V.

The present invention provides another process to copy Lubiprostone crystal V, which comprises the steps of:
(a) dissolving Lubiprostone in a third solvent selected from the group consisting of o-xylene, m-xylene, ethyl ether, isopropyl ether, methyl tert-butyl ether, and mixtures thereof to form a homogenous solution;
(b) lowering the temperature and/or adding a fourth solvent to the homogeneous solution selected from the group consisting of pentane, hexane, heptane, octane, nonane, decane, cyclopentane, cyclohexane, cycloheptane, and mixtures thereof;
(c) adding a seed crystal of Lubiprostone crystal V;
(d) stirring until a precipitate is formed;
(e) filtering out the precipitate, thereby isolating the Lubiprostone crystal V; and
(f) optionally drying the Lubiprostone crystal V.

In an embodiment of the present invention, the third solvent is selected from the group consisting of o-xylene, m-xylene, ethyl ether, isopropyl ether, methyl tert-butyl ether, and mixtures thereof, preferably isopropyl ether. The volume of the third solvent ranges from about 0.5 ml to about 10 ml, preferably about 1 ml to about 5 ml, and more preferably about 1.5 ml to about 4 ml, per 1 g of the crude Lubiprostone. The crude Lubiprostone can be dissolved in the third solvent at a temperature ranging from about 0° C. to about 80° C., preferably from about 20° C. to about 70° C., and more preferably from room temperature to about 60° C.

In an embodiment of the present invention, the fourth solvent is selected from the group consisting of pentane, hexane, heptane, octane, nonane, decane, cyclopentane, cyclohexane, cycloheptane, and a mixture thereof, and preferably n-pentane, n-hexane, cycloheptane, n-heptane, and mixtures thereof. The volume of the fourth solvent ranges from about 0.5 ml to about 30 ml, preferably about 1 ml to about 15 ml, and more preferably about 2 ml to about 10 ml, per 1 ml of the third solvent. The fourth solvent can be added at a temperature ranging from about −50° C. to about 80° C., preferably from about −10° C. to about 60° C., and more preferably from about 0 to about 30° C.

In one embodiment of the present invention, the temperature of the homogenous solution is lowered to a temperature ranging from about −30° C. to about 40° C., preferably about −10° C. to about 30° C., and more preferably about 10° C. to about 25° C.

The precipitation of crystal can be carried out at a temperature ranging from about −10° C. to about 40° C., preferably about 0° C. to about 30° C., and more preferably about 10° C. to about 25° C.

The step of filtering out the precipitate comprises using the fourth solvent or a mixture of the third solvent and the fourth solvent to wash the precipitate. The mixed solvent can contain portions of the third solvent and the fourth solvent in a ratio of about 1:1 to about 1:100, preferably about 1:1 to about 1:10.

The third solvent is the key to determine whether the Lubiprostone crystal V can be directly copied using a seed of Lubiprostone crystal V. For example, the applicant found that when using esters such as isopropyl acetate as the third solvent, Lubiprostone crystal V is rapidly converted into Lubiprostone crystal I; thus, such solvent cannot be used to copy Lubiprostone crystal V. Even using a large amount of Lubiprostone crystal V as seed crystals, it is still impossible to obtain Lubiprostone crystal V. However, the inventors found to their surprise that using o-xylene, m-xylene, ethyl ether, isopropyl ether, or methyl tert-butyl ether as the third solvent renders the Lubiprostone crystal V very stable and highly unlikely to convert to Lubiprostone crystal I. Based on this method, high-purity Lubiprostone crystal V can be obtained in the presence of s seed crystal of Lubiprostone crystal V. If a crystal seed of Lubiprostone crystal V is not added, the method only produces either Lubiprostone crystal I or a mixture of Lubiprostone crystal I and Lubiprostone crystal V. Moreover, regardless of the amount of impurity A that is contained in the crystal seed of Lubiprostone crystal V or in the crude Lubiprostone, the resultant Lubiprostone crystal V is essentially free of impurity A. In other words, the crystallization method effectively removes impurity A from the crude Lubiprostone and the crystal seed of Lubiprostone.

In one embodiment of the present invention, the Lubiprostone crystal V has an XRPD pattern exhibiting its five strongest characteristic peaks at the following 2θ reflection angles: 6.5±0.2°, 13.2±0.2°, 15.6±0.2°, 18.9±0.2°, and 20.2±0.2°. In a preferred embodiment, the XRPD pattern further comprises characteristic peaks at the following 2θ reflection angles: 10.8±0.2°, 14.0±0.2°, 14.8±0.2°, 16.0±0.2°, 17.8±0.2°, 21.0±0.2°, and 21.4±0.2°. More preferably, the XRPD pattern of Lubiprostone crystal V is consistent with FIG. 6. The particular data of Lubiprostone crystal V are shown in Table 1.

TABLE 1

| 2θ angle (°) | d value (Å) | relative intensity (%) |
| --- | --- | --- |
| 6.5 | 13.6 | 100.0 |
| 9.4 | 9.4 | 5.5 |
| 10.8 | 8.2 | 14.6 |
| 11.6 | 7.6 | 7.8 |
| 13.2 | 6.7 | 45.4 |
| 14.0 | 6.3 | 17.5 |
| 14.8 | 6.0 | 24.8 |
| 15.6 | 5.7 | 68.0 |
| 16.0 | 5.5 | 48.5 |
| 17.8 | 5.0 | 42.4 |
| 18.9 | 4.7 | 93.4 |
| 20.2 | 4.4 | 50.5 |
| 21.0 | 4.2 | 43.9 |
| 21.4 | 4.2 | 43.9 |
| 21.7 | 4.1 | 31.1 |
| 22.2 | 4.0 | 20.9 |
| 23.0 | 3.9 | 17.1 |
| 24.2 | 3.7 | 19.8 |
| 24.8 | 3.6 | 16.2 |
| 25.5 | 3.5 | 16.1 |
| 27.1 | 3.3 | 15.0 |
| 27.5 | 3.2 | 15.2 |
| 28.4 | 3.1 | 15.5 |
| 29.1 | 3.1 | 16.8 |
| 29.6 | 3.0 | 15.2 |
| 30.0 | 3.0 | 14.2 |
| 31.1 | 2.9 | 13.8 |
| 32.6 | 2.7 | 12.7 |
| 34.9 | 2.6 | 11.5 |
| 35.4 | 2.5 | 11.8 |
| 37.1 | 2.4 | 11.8 |
| 37.8 | 2.4 | 12.0 |
| 38.6 | 2.3 | 11.2 |
| 40.1 | 2.2 | 11.1 |
| 41.3 | 2.2 | 11.7 |
| 44.3 | 2.0 | 9.7 |
| 45.9 | 2.0 | 8.5 |

In one embodiment, the present invention provides a Lubiprostone crystal V having an XRPD pattern exhibiting its five strongest characteristic peaks at the following 2θ reflection angles: 6.5±0.2°, 13.2±0.2°, 15.6±0.2°, 18.9±0.2°, and 20.2±0.2°, wherein a half peak width of the characteristic peaks at 2θ reflection angles is between about 0.3 and about 2°.

Figure 6:
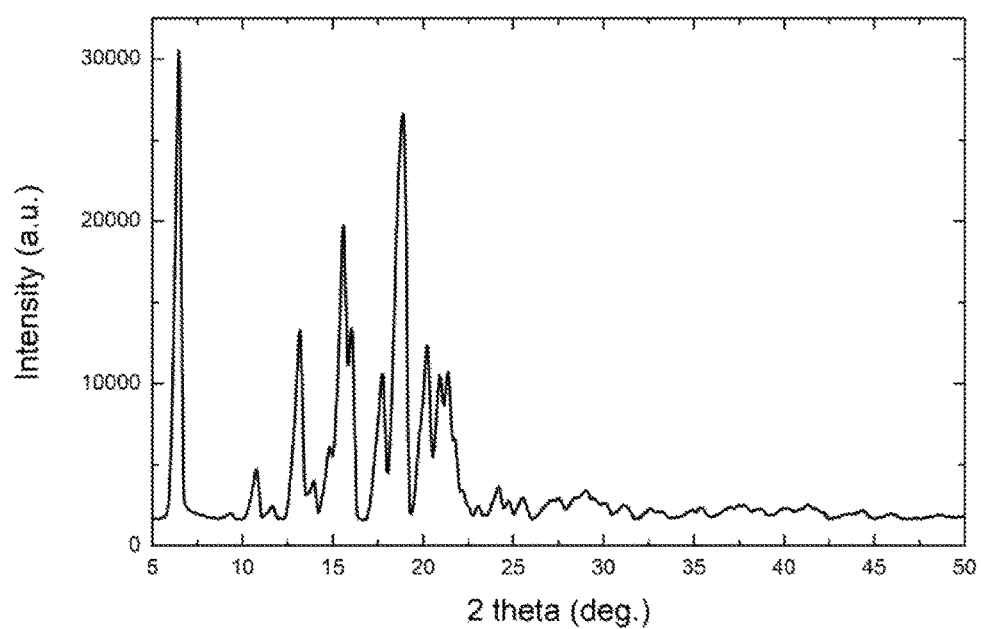
FIG. 6 shows an X-ray powder diffraction (XRPD) pattern of Lubiprostone crystal V.

In one embodiment, the present invention provides a Lubiprostone crystal V having an XRPD pattern substantially as shown in FIG. 6.

Lubiprostone crystal V obtained by the method of the present invention is essentially a single crystalline form, and thus does not contain any other crystalline forms, such as Lubiprostone crystal I. As shown in FIG. 6, there is the only one characteristic peak at the 2θ reflection angles between 2° and 10°, i.e., at 6.5±0.2°, but not 7.6±0.2° (one characteristic peak of Lubiprostone crystal I). In a preferred embodiment, the present invention provides a Lubiprostone crystal V having an XRPD pattern exhibiting its five strongest characteristic peaks at the following 2θ reflection angles: 6.5±0.2°, 13.2±0.2°, 15.6±0.2°, 18.9±0.2°, and 20.2±0.2°, and substantially free of a characteristic peak at 2θ reflection angle of 7.6±0.2°. In the present invention, the term "substantially free of" means that in the XRPD pattern, the peak intensity at 7.6±0.2° is less than 5%, preferably less than 1% of the peak intensity at 6.5±0.2°.

In one embodiment, the present invention provides a Lubiprostone crystal V having a differential scanning calorimetry (DSC) thermogram pattern comprising an endothermic peak with a peak onset temperature of 60.60°±1° C. and a peak maximum of 64.7±1° C.

Figure 7:
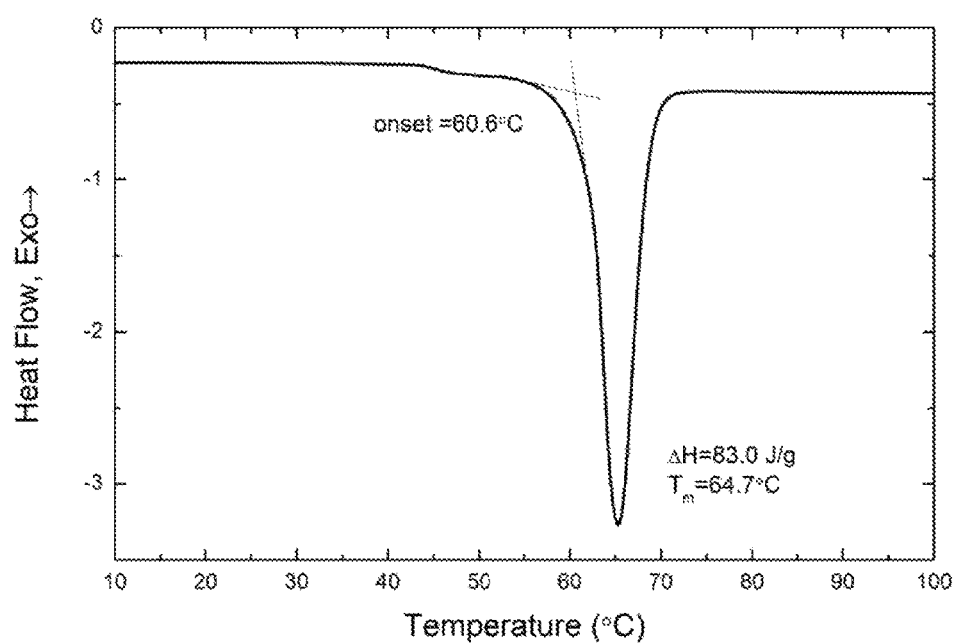
FIG. 7 shows a differential scanning calorimetry (DSC) thermogram pattern of Lubiprostone crystal V.

In one embodiment, the present invention provides a Lubiprostone crystal V having a DSC thermogram pattern substantially as shown in FIG. 7.

In one embodiment, the present invention provides a Lubiprostone crystal V having a 1% KBr Fourier transform infrared (FTIR) spectrum comprising peaks, in terms of $cm^{-1}$, at 3388±4, 2938±4, 2872±4, 1729±4, 1713±4, 1415±4, 1247±4, 1222±4, 1207±4, 1180±4, 1105±4, 1091±4, 1060±4, 1006±4, 987±4, 918±4, 761±4, and 723±4.

Figure 8:
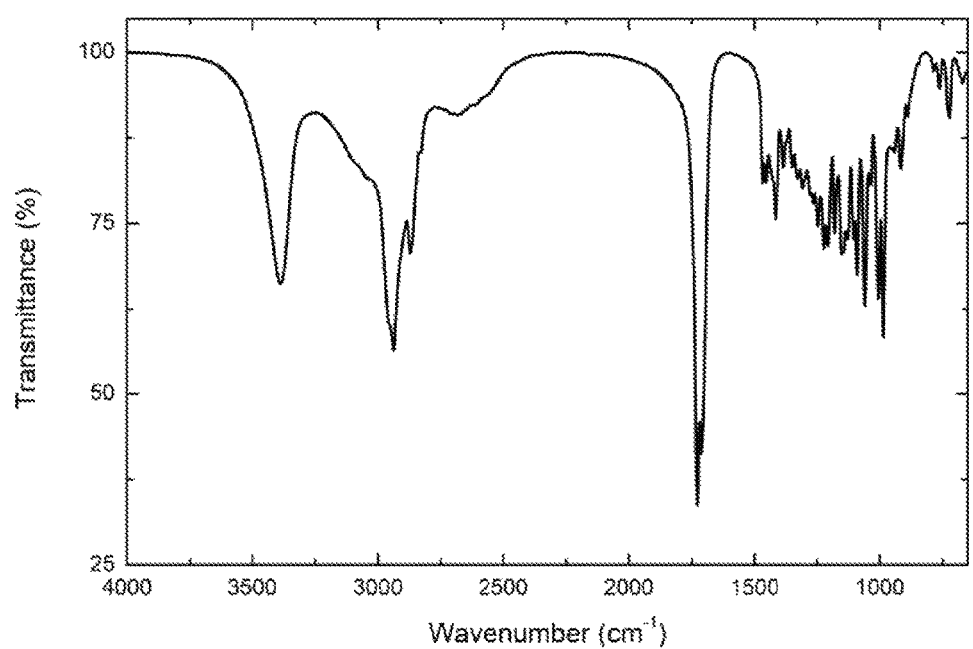
FIG. 8 shows a Fourier Transform Infrared (FTIR) spectrum of Lubiprostone crystal V.

In one embodiment, the present invention provides a Lubiprostone crystal V having a 1% KBr FTIR spectrum substantially as shown in FIG. 8.

The Lubiprostone crystal V of the present invention contains no more than about 0.3%, preferably no more than about 0.2%, preferably no more than about 0.1% of impurity A, and more preferably contains a non-detectable level of impurity A as determined by HPLC method, the detection limit of HPLC method being more than 0.02%.

In addition, the Lubiprostone crystal V of the present invention shows good stability, with no other crystalline forms or degraded products of impurity A, even after six months of storage at normal temperatures for Lubiprostone (about −20° C.).

Lubiprostone Crystal VI and Preparation Thereof

In one embodiment, the process for preparing Lubiprostone crystal VI comprises the steps of:
(a) dissolving crude Lubiprostone in p-xylene to form a homogenous solution;
(b) lowering the temperature and/or adding a fifth solvent to the homogenous solution selected from the group consisting of pentane, hexane, heptane, octane, nonane, decane, cyclopentane, cyclohexane, cycloheptane, and mixtures thereof;
(c) optionally adding a seed crystal of Lubiprostone crystal VI;
(d) stirring the mixture until precipitation occurs thereby forming a precipitate;
(e) filtering out the precipitate, thereby isolating the Lubiprostone crystal VI; and
(f) optionally drying the Lubiprostone crystal VI.

In one embodiment, the volume of p-xylene ranges from about 0.5 ml to about 10 ml, preferably about 1 ml to about 5 ml, and preferably about 1.5 ml to about 4 ml, per 1 g of the crude Lubiprostone. The crude Lubiprostone can be dissolved in p-xylene at a temperature ranging from about 10° C. to about 80° C., preferably from about 20° C. to about 70° C., and more preferably from about room temperature to about 60° C.

In one embodiment, the fifth solvent is selected from the group consisting of pentane, hexane, heptane, octane, nonane, decane, cyclopentane, cyclohexane, cycloheptane, and mixtures thereof, and preferably n-pentane, n-hexane, cycloheptane, n-heptane, and mixtures thereof. The volume of the fifth solvent ranges from about 0.5 ml to about 30 ml, preferably about 1 ml to about 15 ml, and preferably about 2 ml to about 10 ml, per 1 ml of p-xylene. This solvent can be added at a temperature ranging from about 10° C. to about 80° C., preferably from about 15° C. to about 60° C., and more preferably from about 20° C. to about 50° C.

In one embodiment of the present invention, the temperature of the homogenous solution is lowered to a temperature ranging from about 0° C. to about 40° C., preferably from about 15° C. to about 30° C., and more preferably from about 15° C. to about 25° C.

The precipitation of the crystal may be performed at a temperature ranging from about 10° C. to about 40° C., preferably about 12° C. to about 30° C., and more preferably about 15° C. to about 25° C.

The filtering out of the precipitate comprises using the fifth solvent or a mixture of p-xylene and the fifth solvent to wash the precipitate. In the mixed solvent, the quantities of p-xylene and the fifth solvent is in a ratio of about 1:1 to about 1:100, preferably about 1:1 to about 1:10.

Lubiprostone crystal VI obtained by the aforementioned method of the present invention is essentially a single crystalline form, and contains a lower amount or even is substantially free of impurity A.

In the present invention, Lubiprostone crystal VI has an XRPD pattern exhibiting its five strongest characteristic peaks at the following 2θ reflection angles: 7.5±0.2°, 10.3±0.2°, 13.9±0.2°, 18.7±0.2°, and 21.1±0.2°. More preferably, the XRPD pattern of Lubiprostone crystal VI is consistent with FIG. 9. The particular data of Lubiprostone crystal VI are shown in Table 2

TABLE 2

| 2θ angle (°) | d value (Å) | relative intensity % |
|---|---|---|
| 6.2 | 14.2 | 19.5 |
| 7.5 | 11.9 | 66.7 |
| 10.3 | 8.6 | 100.0 |
| 11.2 | 7.9 | 11.3 |
| 11.8 | 7.5 | 10.0 |
| 12.5 | 7.1 | 20.8 |
| 12.9 | 6.9 | 13.3 |
| 13.9 | 6.3 | 64.3 |
| 14.8 | 6.0 | 79.5 |
| 15.3 | 5.8 | 25.5 |
| 17.0 | 5.2 | 27.2 |
| 18.7 | 4.7 | 84.1 |
| 19.3 | 4.6 | 46.6 |
| 21.1 | 4.2 | 67.5 |
| 22.3 | 4.0 | 41.4 |
| 23.1 | 3.9 | 29.9 |
| 23.8 | 3.7 | 29.9 |
| 26.2 | 3.4 | 20.7 |
| 28.9 | 3.1 | 21.1 |
| 31.4 | 2.9 | 22.0 |
| 33.5 | 2.7 | 17.6 |
| 37.9 | 2.4 | 18.1 |
| 41.1 | 2.2 | 17.8 |
| 45.0 | 2.0 | 12.2 |
| 47.3 | 1.9 | 10.5 |

Figure 10:
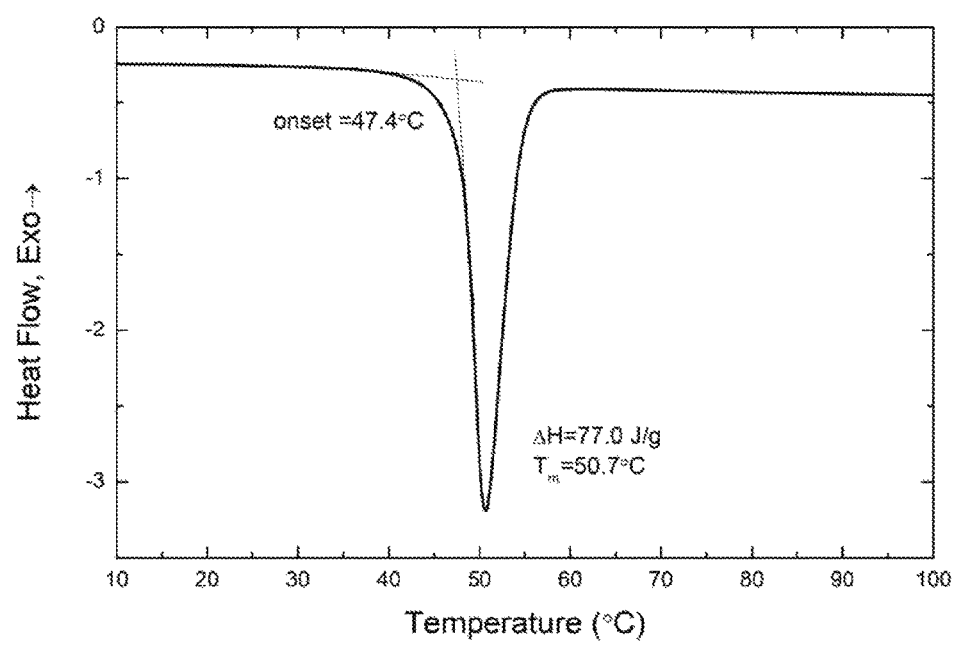
FIG. 10 shows a differential scanning calorimetry (DSC) thermogram of Lubiprostone crystal VI.
Figure 11:
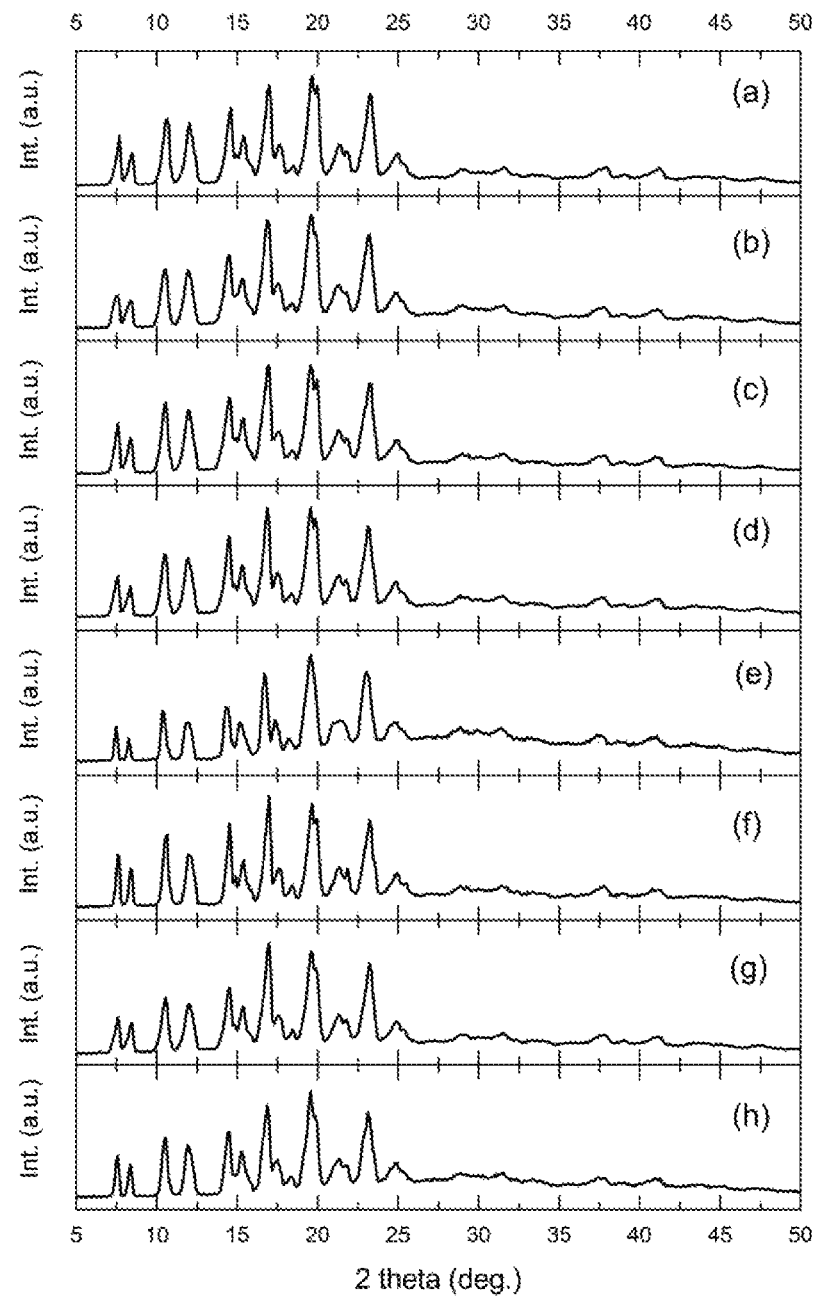
FIG. 11 shows XRPD patterns of the Lubiprostone crystals which were prepared from the isopropyl acetate/heptane system at (a) 30° C., 18 h, 100 rpm; (b) 25° C., 18 h, 100 rpm; (c) 20° C., 18 h, 100 rpm; (d) 10° C., 18 h, 100 rpm; (e) 0° C., 18 h, 100 rpm; (f) 20° C., 18 h, 50 rpm; (g) 20° C., 18 h, 200 rpm; and (h) 20° C., 18 h, 250 rpm.

In one embodiment, the present invention provides a Lubiprostone crystal VI having a DSC thermogram pattern comprising an endothermic peak with a peak onset temperature of approximately 47.4±1° C. and a peak maximum of approximately 50.7±1° C. In a preferred embodiment, the present invention provides a Lubiprostone crystal VI having a DSC thermogram pattern substantially as shown in FIG. 10.

The Lubiprostone crystal VI of the present invention contains no more than about 0.3%, preferably no more than about 0.2%, preferably no more than about 0.1% of impurity A, and more preferably contains a non-detectable level of impurity A as determined by HPLC method, the detection limit of HPLC method being more than 0.02%.

The following examples are used to further illustrate the present invention, but are not intended to limit the scope of the present invention. Any modifications or alterations that can be easily accomplished by persons skilled in the art fall within the scope of the disclosure of the specification and the appended claims.

EXAMPLES

X-ray Powder Diffraction (XRPD) Analysis: The XRPD patterns were collected on a Bruker D2 PHASER diffractometer with fixed divergence slits and 1D LYNXEYE detector. The samples (ca. 100 mg) were flatly placed on a sample holder. The prepared samples were analyzed over a 2θ range from 5° to 50° with step size of 0.02 degrees and step time of 1 second using $CuK_\alpha$ radiation at a power of 10 mA and 30 kV. The $CuK_\beta$ radiation was removed by a divergent beam nickel filter.

Differential Scanning Calorimetry (DSC) Analysis: The DSC patterns were collected on a TA DISCOVERY DSC25 instrument. The samples (ca. 5 mg) were weighed into an aluminum pan with a crimping closed aluminum lid. The prepared samples were analyzed from 10° C. to 100° C. at scan rate of 10° C./min under a flow of nitrogen (ca. 50 ml/min). The melting point temperature and heat of fusion were calibrated by indium (In) before measurement.

Fourier Transform Infrared (FTIR) Analysis: The FTIR spectra were collected on a Perkin Elmer SPECTRUM 100 instrument. The samples were mixed with potassium bromide (KBr) in an approximately 1:100 ratio (w/w) using an agate mortar and pestle. The mixture was compressed in a pellet die at a pressure of about 10 to 13 tonnes for 2 minutes. The resulting disk was scanned 4 times against a collected background from 4000 $cm^{-1}$ to 650 $cm^{-1}$ at a resolution of 4 $cm^{-1}$. The data was baseline corrected and normalized.

Example 1

Preparation of Crude Lubiprostone

4-Methoxybenzyl 7-[(2R, 4aR, 5R, 7aR)-2-(1,1-difluoropentyl)-octahydro-2-hydroxy-6-oxocyclopenta[b]pyran-5-yl]heptanoate (60 g, 117.5 mmol, enantiomeric purity ≥99%) was dissolved in 600 ml ethyl acetate and followed by addition of 5% palladium on charcoal under hydrogen for 3 hours. Then, the reaction mixture was filtered with celite pad. The solvent was evaporated off under vacuum. The crude product was purified by chromatography on silica gel using a mixture of hexane and ethyl acetate as a gradient eluent to obtain 40 g oily Lubiprostone. HPLC analysis of the product showed that 1.1% impurity A was found.

Example 2

Preparation of Lubiprostone Crystal VI

Figure 9:
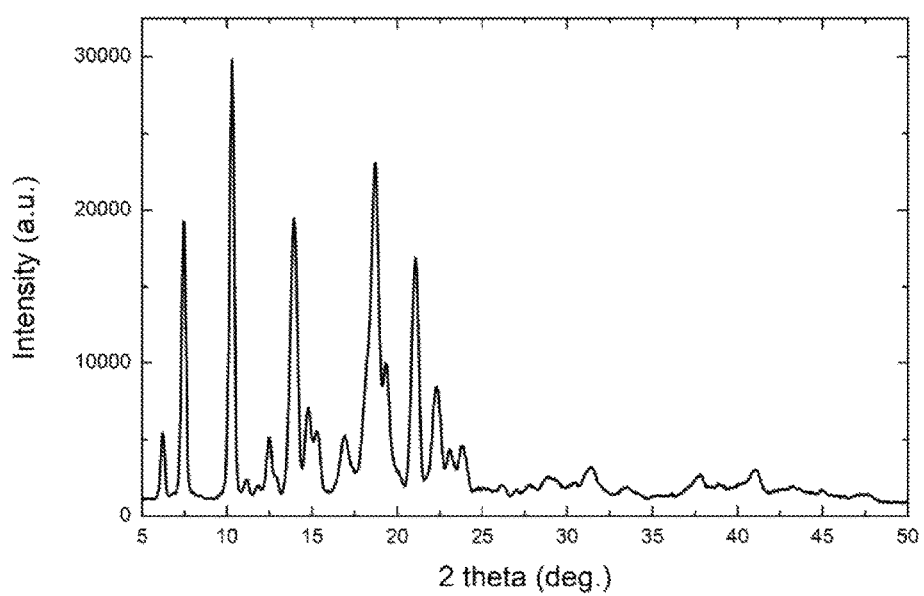
FIG. 9 shows an X-ray powder diffraction (XRPD) pattern of Lubiprostone crystal VI.

Oily Lubiprostone (0.51 g, from Example 1) and p-xylene (1.0 ml) were heated at 40° C. for dissolution and then cooled to room temperature. A solvent of n-pentane (1.0 ml) was added slowly dropwise and the mixture was stirred in an ice-water bath for 1 hour until solid precipitation occurred. The resulting suspension was filtered and rinsed, and then dried under high vacuum at room temperature for 4 hours to give 0.38 g Lubiprostone crystal VI. HPLC analysis of the product showed that no impurity A was found. The XRPD and DSC results were as shown in FIG. 9 and FIG. 10.

Example 3

Preparation of Lubiprostone Crystal VI

Oily Lubiprostone (0.52 g, from Example 1) and p-xylene (1.3 ml) were heated at 40° C. for dissolution and then cooled to room temperature. The mixture was stirred in an ice-water bath for 1 hour until solid precipitation occurred. The resulting suspension was filtered and rinsed, and then dried under high vacuum at room temperature for 4 hours to give 0.41 g Lubiprostone crystal VI. HPLC analysis of the product showed that no impurity A was found. The XRPD and DSC results were as shown in FIG. 9 and FIG. 10.

Example 4

Preparation of Lubiprostone Crystal VI

Oily Lubiprostone (0.50 g, from Example 1) and p-xylene (1.0 ml) were heated at 40° C. for dissolution and then cooled to room temperature. A solvent of n-pentane (1.0 ml) was added slowly dropwise and the mixture was stirred for 1 hour until solid precipitation occurred. Afterwards, the resulting suspension was filtered and rinsed, and then dried under high vacuum at room temperature for 4 hours to give 0.41 g Lubiprostone crystal VI. HPLC analysis of the product showed that no impurity A was found. The XRPD and DSC results were the same as shown in FIG. 9 and FIG. 10.

Example 5

Preparation of Lubiprostone Crystal VI

Oily Lubiprostone (0.20 g, from Example 1) and p-xylene (1.0 ml) were heated at 40° C. for dissolution and then cooled to room temperature. A solvent of n-hexane (1.0 ml) was added slowly dropwise and the mixture was stirred for 1 hour until solid precipitation occurred. The resulting suspension was filtered and rinsed, and then dried under high vacuum at room temperature for 4 hours to 0.14 g give Lubiprostone crystal VI. HPLC analysis of the product showed that no impurity A was found. The XRPD and DSC results were as shown in FIG. 9 and FIG. 10.

Example 6

Preparation of Lubiprostone Crystal V

Oily Lubiprostone (0.20 g, from Example 1) and o-xylene (0.5 ml) were heated at 40° C. for dissolution and then cooled to room temperature. A solvent of n-pentane (1.0 ml) was added slowly dropwise and the mixture was stirred in ice water bath for 2 hours until a phase-separated fluid formed. The phase-separated fluid was then separated and evaporated under vacuum at ambient temperature until solid precipitation occurred. The resulting precipitate was washed with 1.0 ml n-pentane, and isolated by filtration and dried under vacuum at ambient temperature to give 0.10 g Lubiprostone crystal V. HPLC analysis of the product showed that 0.21% impurity A was found. The XRPD, DSC, and FTIR results were as shown in FIG. 6, FIG. 7 and FIG. 8.

Example 7

Preparation of Lubiprostone Crystal V

Oily Lubiprostone (0.20 g, from Example 1) and o-xylene (0.5 ml) were heated at 40° C. for dissolution and then cooled to room temperature. A solvent of n-pentane (1.0 ml) was added slowly dropwise and the mixture stirred for 2 hours until a phase-separated fluid formed. The phase-separated fluid was then separated and evaporated under vacuum at ambient temperature until solid precipitation occurred. The resulting precipitate was washed with 1.0 ml n-pentane, and isolated by filtration and dried under vacuum at ambient temperature to give 0.12 g Lubiprostone. The XRPD, DSC, and FTIR results were shown in FIG. 6, FIG. 7 and FIG. 8. HPLC analysis of the product showed that 0.18% impurity A was found.

Example 8

Preparation of Lubiprostone Crystal V

Oily Lubiprostone (0.20 g, from Example 1) and m-xylene (0.5 ml) were heated at 40° C. for dissolution and then cooled to room temperature. A solvent of n-heptane (1.0 ml) was added slowly dropwise and stirred for half an hour until a phase-separated fluid formed. The phase-separated fluid was then separated and evaporated under vacuum at ambient temperature until solid precipitation occurred. The resulting precipitate was washed with 1.0 ml n-heptane, and isolated by filtration and dried under vacuum at ambient temperature to give 0.11 g Lubiprostone. The XRPD, DSC, and FTIR results were as shown in FIG. 6, FIG. 7 and FIG. 8. HPLC analysis of the product showed that 0.1% impurity A was found.

Example 9

Copy of Lubiprostone Crystal V

Oily Lubiprostone (0.50 g, from Example 1) and o-xylene (2.0 ml) were heated at 40° C. for dissolution and then cooled to room temperature. A solvent of n-pentane (4.0 ml) was added slowly dropwise, and then seed crystal (10 mg, crystal V as prepared in Example 6) was added and the mixture was stirred for 1 hour until solid precipitation occurred. The resulting suspension was filtered and rinsed, and then dried under high vacuum at room temperature for 4 hours to give Lubiprostone Crystal V (0.32 g). The XRPD, DSC, and IR results were as shown in FIG. 6, FIG. 7 and FIG. 8. HPLC analysis of the product showed that no impurity A was found.

Example 10

Copy of Lubiprostone Crystal V

Oily Lubiprostone (0.20 g, from Example 1) and isopropyl ether (0.6 ml) were heated at 40° C. for dissolution and then cooled to room temperature. A solvent of n-heptane (0.6 ml) was added slowly dropwise, and then seed crystal (10 mg, crystal V as prepared in Example 6) was added and the mixture was stirred for 1 hour until solid precipitation occurred. The resulting suspension was filtered and rinsed, and then dried under high vacuum at room temperature for half an hour to give Lubiprostone crystal V (0.11 g). The XRPD, DSC, and IR results were as shown in FIG. 6, FIG. 7 and FIG. 8. HPLC analysis of the product showed that no impurity A was found.

Example 11

Copy of Lubiprostone Crystal V

Oily Lubiprostone (0.20 g, from Example 1) and methyl tert-butyl ether (0.6 ml) were heated at 40° C. for dissolution and then cooled to room temperature. A solvent of n-pentane (0.6 ml) was added slowly dropwise, and then seed crystal (10 mg, crystal V as prepared in Example 6) was added and the mixture was stirred for 1 hour until solid precipitation occurred. The resulting suspension was filtered and rinsed, and then dried under high vacuum at room temperature for half an hour to give Lubiprostone crystal V (0.10 g). The XRPD, DSC, and IR results were as shown in FIG. 6, FIG. 7 and FIG. 8. HPLC analysis of the product showed that no impurity A was found.

Example 12

Copy of Lubiprostone Crystal V

Oily Lubiprostone (0.20 g, from Example 1) and ethyl ether (0.6 ml) were heated at 40° C. for dissolution and then cooled to room temperature. A solvent of n-hexane (0.8 ml) was added slowly dropwise, and then seed crystal (10 mg, crystal V as prepared in Example 6) was added and the mixture was stirred for 1 hour until solid precipitation occurred. The resulting suspension was filtered and rinsed, and then dried under high vacuum at room temperature for half an hour to give Lubiprostone crystal V (0.14 g). The XRPD, DSC, and IR results were as shown in FIG. 6, FIG. 7 and FIG. 8. HPLC analysis of the product showed that no impurity A was found.

Example 13

Reproduction of Lubiprostone Crystal II According to Paragraph [0038] of US 2010/056808

Oily Lubiprostone (0.20 g, from Example 1, enantiomeric purity >99%) and isopropyl acetate (0.16 ml, 0.8 parts) were heated at 40° C. for dissolution and then cooled to 30° C., 25° C., 20° C., 10° C., and 0° C., respectively. Heptane (0.84 ml, 4.2 parts) was added slowly dropwise, and the mixture was stirred (at 50, 100, 200, or 250 rpm) for 18 hours until solid precipitation occurred at 30° C., 25° C., 20° C., 10° C., and 0° C., respectively. The resulting suspension was filtered and rinsed, and then dried under high vacuum at room temperature to give Lubiprostone crystal II. The XRPD results are shown in FIGS. 11(a) to 11(h).

Figure 2:
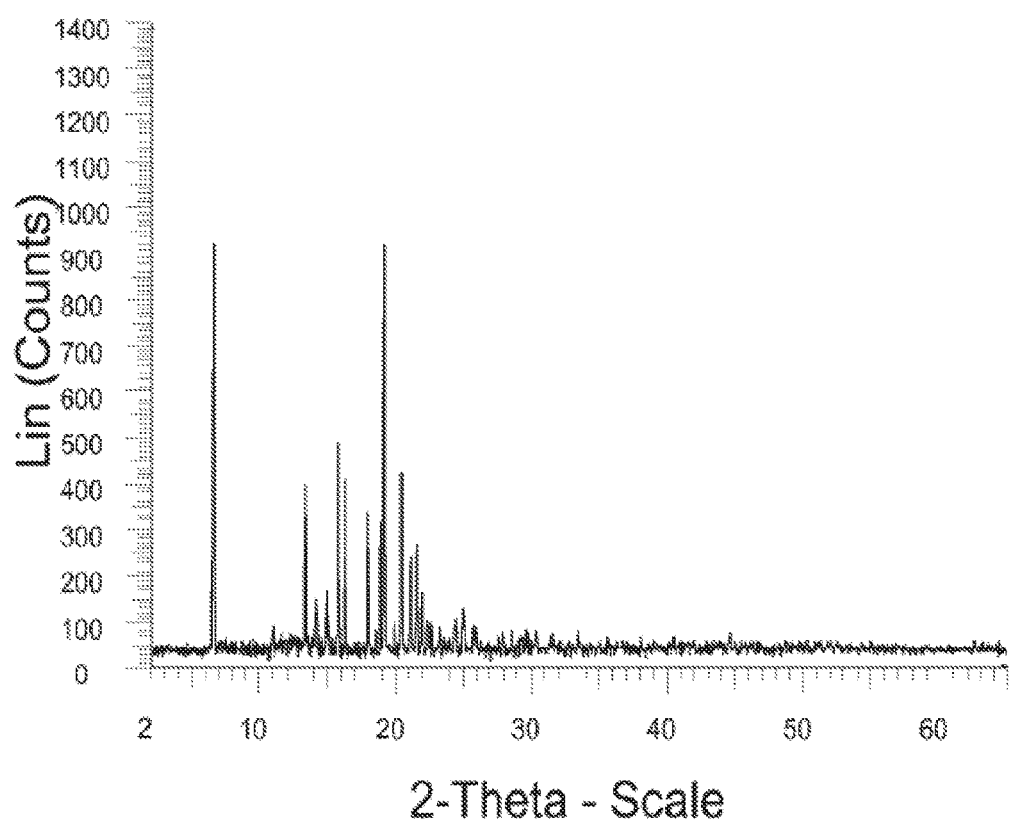
FIG. 2 is an ideal X-ray powder diffraction (XRPD) pattern calculated from the single crystal data of Lubiprostone crystal II.
Figure 3:
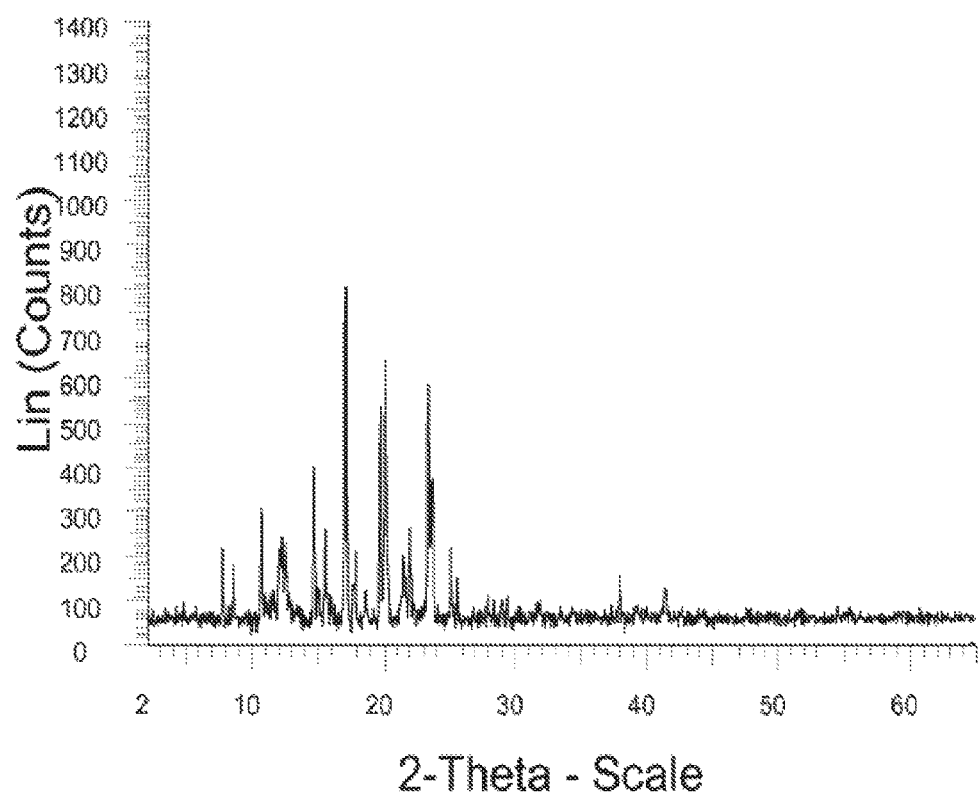
FIG. 3 is another ideal X-ray powder diffraction (XRPD) pattern calculated from the single crystal data of Lubiprostone crystal II.
Figure 4:
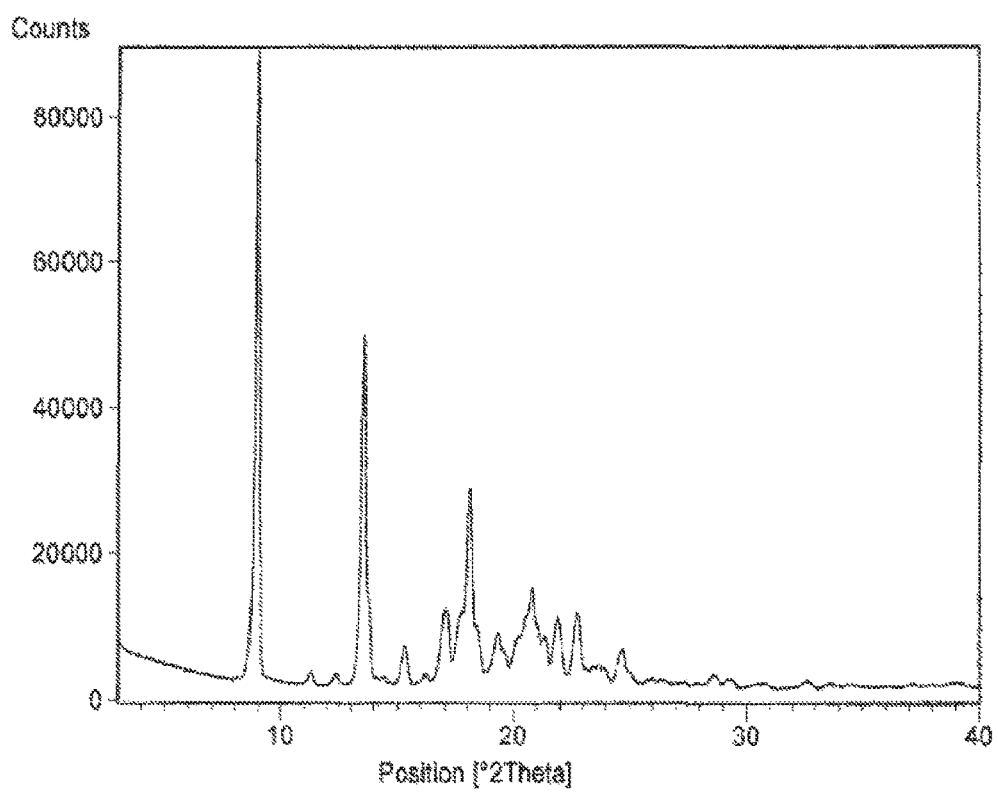
FIG. 4 shows an X-ray powder diffraction (XRPD) pattern of Lubiprostone crystal III.
Figure 5:
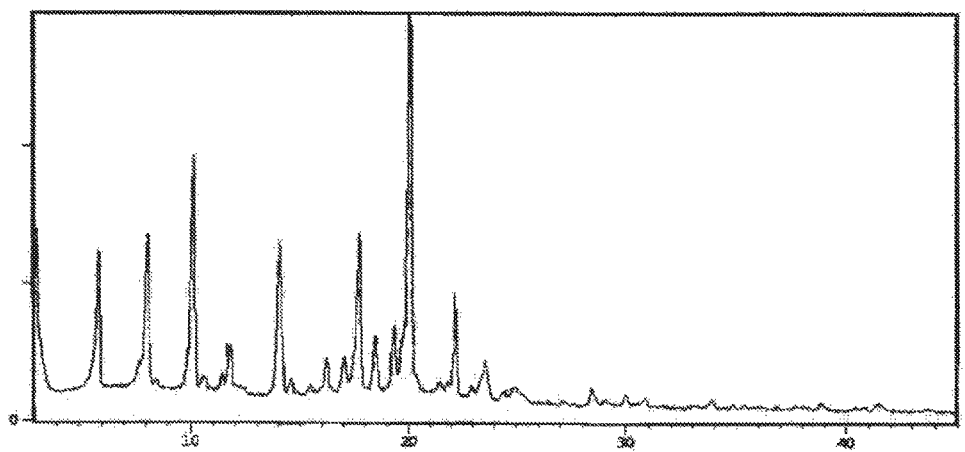
FIG. 5 shows an X-ray powder diffraction (XRPD) pattern of Lubiprostone crystal IV.

As shown in FIGS. 11(a) to 11(h), only the patterns depicted in FIG. 1 and FIG. 3 (Lubiprostone crystal I), but not the pattern depicted in FIG. 2, can be seen in the XRPD patterns of FIGS. 11(a) to 11(h). The results demonstrate that FIG. 1 and FIG. 3 (i.e., FIG. 3 of US 2010/056808) show the XRPD patterns of the crystalline forms of Lubiprostone, and FIG. 2 (i.e., FIG. 2 of US 2010/056808) shows the XRPD pattern of an enantiomorph of Lubiprostone. This is because the oil Lubiprostone used in this example only contains less than 1% enantiomer, which is lower than the detection limit of the XRPD analysis, so the pattern of the enantiomorph of Lubiprostone cannot be seen in all of the XRPD patterns. Given this, FIG. 2 of US 2010/0056808 shows the XRPD pattern of the enantiomorph of Lubiprostone, rather than the crystalline form of Lubiprostone.

Therefore, although the XRPD pattern of Lubiprostone crystal V shown in FIG. 6 is similar to that in FIG. 2, the polymorph A shown in FIG. 2 of US 2010/056808 is an enantiomorph of Lubiprostone, rather than Lubiprostone crystal V which is a single crystalline form. In addition, it can be seen that a major difference between the patterns shown in FIG. 2 and FIG. 6 is the half peak width of the characteristic peaks at 2θ reflection angles. The half peak width of Lubiprostone crystal V at 2θ reflection angles is between about 0.3° and about 2°, but the half peak width shown in FIG. 2 at 2θ reflection angles is below 0.3°, which means that the average crystal sizes of the Lubiprostone crystal V and the enantiomorph of Lubiprostone are different.

Example 14

Crystal Form Transformation of Lubiprostone

Lubiprostone crystal V (0.20 g, from Example 9) was added to a mixture of isopropyl acetate (0.16 ml) and heptane (0.84 ml)(i.e., the solvent system for crystallization of US 2010/056808), and the mixture was stirred at 20° C. for 2 hours. The resulting suspension was filtered and rinsed, and then dried under high vacuum at room temperature to give Lubiprostone crystal I. The XRPD results are shown in FIGS. 12(a) and 12(b).

Figure 12:
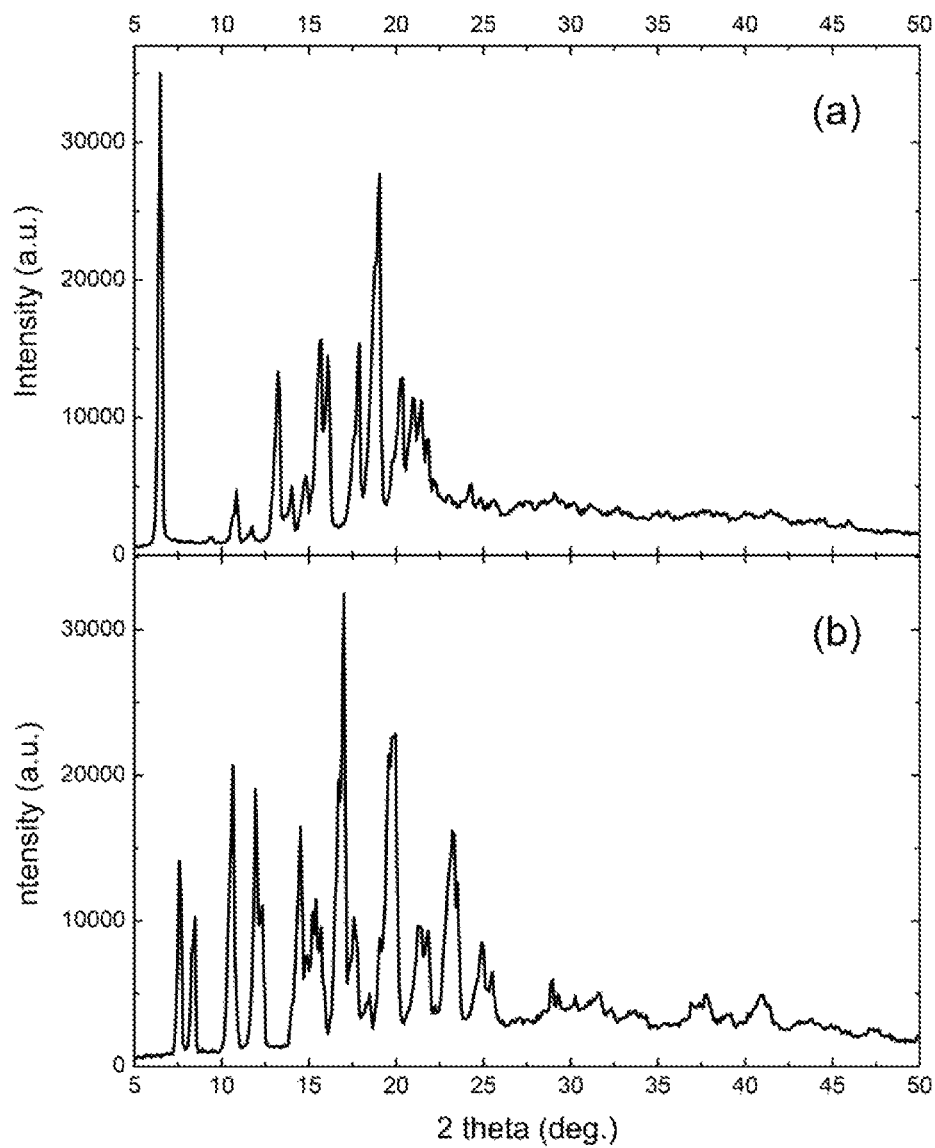
FIG. 12 shows the crystal form transformation of Lubiprostone crystal V which was stirred in isopropyl acetate/heptane for (a) 20° C., 0 h; and (b) 20° C., 2 h.

As shown in FIGS. 12(a) and 12(b), the crystalline form of Lubiprostone crystal V has been completely converted to the crystalline form shown in FIG. 1 and FIG. 3 (Lubiprostone crystal I) within only two hours. The results prove that Lubiprostone crystal II obtained from US 2010/056808 does not contain any Lubiprostone crystal V because Lubiprostone crystal V cannot be present under the crystallization conditions of US 2010/056808 over 18 hours. Therefore, the Lubiprostone crystal V is a novel crystalline form of Lubiprostone, and the crystalline form shown in FIG. 2 found in the unit cell of Lubiprostone crystal II by optical microscope is an enantiomorph of Lubiprostone, rather than Lubiprostone crystal V.

What is claimed is:

1. A Lubiprostone crystal VI having an X-ray powder diffraction (XRPD) pattern exhibiting its five strongest characteristic peaks at the following 2θ reflection angles: 7.5±0.2°, 10.3±0.2°, 13.9±0.2°, 18.7±0.2°, and 21.1±0.2°.

2. The Lubiprostone crystal VI of claim 1, wherein the XRPD pattern further comprises characteristic peaks at the following 2θ reflection angles: 6.2±0.2°, 12.5±0.2°, 14.8±0.2°, 15.3±0.2°, 17.0±0.2°, 19.3±0.2°, 22.3±0.2°, 23.8±0.2°, and 26.2±0.2°.

3. The Lubiprostone crystal VI of claim 2, wherein the XRPD pattern is substantially shown in FIG. 9.

4. The Lubiprostone crystal VI of claim 1 having a differential scanning calorimetry (DSC) thermogram pattern comprising an endothermic peak with a peak onset temperature of about 47.4±1° C. and a peak maximum of about 50.7±1° C.

5. The Lubiprostone crystal VI of claim 4, wherein the DSC thermogram pattern is substantially shown in FIG. 10.

6. A method for preparing the Lubiprostone crystal VI of claim 1, which comprises the steps of:
dissolving Lubiprostone in p-xylene to form a homogenous solution;
lowering the temperature and/or adding a solvent selected from the group consisting of pentane, hexane, heptane, octane, nonane, decane, cyclopentane, cyclohexane, cycloheptane, and mixtures thereof; and
stirring until a precipitate is formed.

7. The method of claim 6, further comprising the step of adding a seed crystal of Lubiprostone crystal VI, prior to the stirring step.

8. The method of claim 6, further comprising the steps of:
filtering out the precipitate, thereby isolating the Lubiprostone crystal VI; and
optionally drying the Lubiprostone crystal VI.

9. A Lubiprostone crystal V having an X-ray powder diffraction (XRPD) pattern exhibiting its five strongest characteristic peaks at the following 2θ reflection angles: 6.5±0.2°, 13.2±0.2°, 15.6±0.2°, 18.9±0.2°, and 20.2±0.2°, wherein a half peak width of the characteristic peaks at 2θ reflection angles is between about 0.3° and about 2°.

10. The Lubiprostone crystal V of claim 9, wherein the XRPD pattern is substantially free of a characteristic peak at 2θ reflection angle of 7.6±0.2°.

11. The Lubiprostone crystal V of claim 10, wherein the XRPD pattern is substantially shown in FIG. 6.

12. The Lubiprostone crystal V of claim 9 having a differential scanning calorimetry (DSC) thermogram pattern comprising an endothermic peak with a peak onset temperature of 60.6±1° C. and a peak maximum of 64.7±1° C.

13. The Lubiprostone crystal V of claim 12, wherein the DSC thermogram pattern is substantially shown in FIG. 7.

14. The Lubiprostone crystal V of claim 9 having a 1% KBr Fourier transform infrared (FTIR) spectrum comprising peaks, in terms of cm$^{-1}$, at 3388±4, 2938±4, 2872±4, 1729±4, 1713±4, 1415±4, 1247±4, 1222±4, 1207±4, 1180±4, 1105±4, 1091±4, 1060±4, 1006±4, 987±4, 918±4, 761±4, and 723±4.

15. The Lubiprostone crystal V of claim 14, wherein the FTIR spectrum is substantially shown in FIG. 8.

16. A method for preparing the Lubiprostone crystal V of claim 9, which comprises the steps of:
dissolving Lubiprostone in a first solvent selected from the group consisting of o-xylene, m-xylene, and a mixture thereof to form a homogenous solution;
lowering the temperature and/or adding to the homogeneous solution a second solvent selected from the group consisting of pentane, hexane, heptane, octane, nonane, decane, cyclopentane, cyclohexane, cycloheptane, and mixtures thereof until a phase-separated fluid is formed at the bottom;
pipetting out an upper clear solution and collecting the remaining phase-separated fluid; and
evaporating off the phase-separated fluid under high vacuum until a precipitate is formed.

17. The method of claim 16, further comprising the step of optionally adding a seed crystal of Lubiprostone crystal V between the pipetting step and the evaporation step.

18. The method of claim 16, further comprising the steps of:
adding the second solvent for rinsing the precipitate;
filtering out the precipitate, thereby isolating the Lubiprostone crystal V; and
optionally drying the Lubiprostone crystal V.

19. A method for preparing the Lubiprostone crystal V of claim 9, which comprises the steps of:
dissolving Lubiprostone in a third solvent selected from the group consisting of o-xylene, m-xylene, ethyl ether, isopropyl ether, methyl tert-butyl ether, and mixtures thereof to form a homogenous solution;
lowering the temperature and/or adding a fourth solvent selected from the group consisting of pentane, hexane, heptane, octane, nonane, decane, cyclopentane, cyclohexane, cycloheptane, and mixtures thereof;
adding a seed crystal of Lubiprostone crystal V; and
stirring until a precipitate is formed.

20. The method of claim 19, further comprising the steps of:
filtering out the precipitate, thereby isolating the Lubiprostone crystal V; and
optionally drying the Lubiprostone crystal V.

* * * * *